Figure 1:
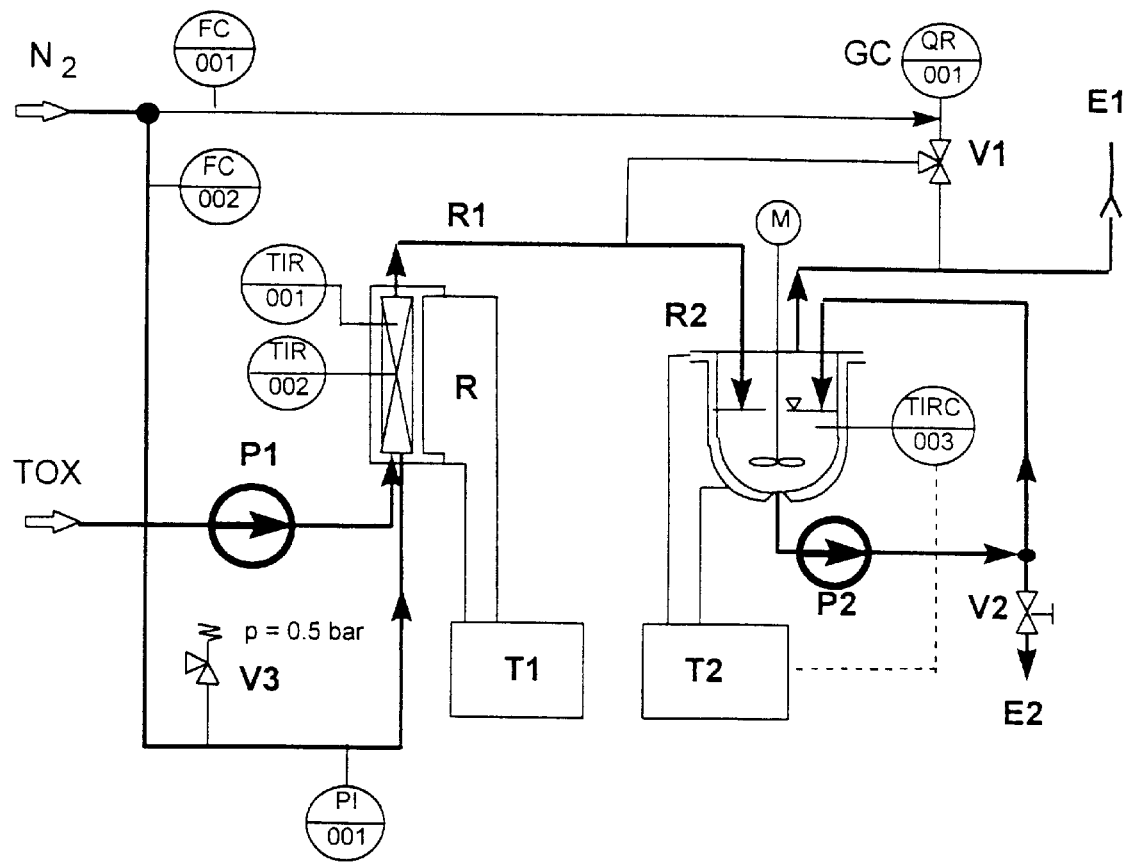

§
United States Patent [19]

Kniep et al.

[11] Patent Number: 6,121,467

[45] Date of Patent: Sep. 19, 2000

[54] SEPARATING OFF TRIOXANE FROM GASEOUS MIXTURES WITH FORMALDEHYDE

[75] Inventors: Hagen Kniep, Frankfurt; Christine Meister, Sulzbach; Elke Schweers, Bad Soden; Ioannis Nicolaou, Kelkheim; Dirk Scheid, Waldems, all of Germany

[73] Assignee: Ticona GmbH, Germany

[21] Appl. No.: 09/360,208

[22] Filed: Jul. 23, 1999

[30] Foreign Application Priority Data

Jul. 25, 1998 [DE] Germany .......................... 198 33 620

[51] Int. Cl.$^7$ ................................................. C07D 323/06

[52] U.S. Cl. ............................................................ 549/368

[58] Field of Search ................................................ 549/368

[56] References Cited

U.S. PATENT DOCUMENTS 5,766,424  6/1998  Arnold et al. .......................... 203/74
5,872,263  2/1999  Hoffmockel et al. .................. 549/368

FOREIGN PATENT DOCUMENTS 35 08 668 A1  10/1985  Germany .
1 245 990 A    9/1971  United Kingdom .

*Primary Examiner*—Ba K. Trinh
*Attorney, Agent, or Firm*—Connolly, Bove, Lodge & Hutz LLP

[57] ABSTRACT

The invention relates to a method for separating a gaseous mixture comprising formaldehyde and trioxane, wherein at least some of the formaldehyde and the trioxane are dissolved from the mixture in a alcohol-containing liquid and the trioxane is crystallized from the solution thus obtained and is separated.

10 Claims, 2 Drawing Sheets

SEPARATING OFF TRIOXANE FROM GASEOUS MIXTURES WITH FORMALDEHYDE

The invention relates to a method for separating a gaseous mixture comprising formaldehyde and trioxane.

The manufacture of engineering plastics such as polyacetals or polyoxymethylene requires highly pure trioxane. The quality of the plastic, especially the degree of polymerization, is determined not only by the polymerization conditions but also, most importantly, by the purity of the trioxane.

Various processes for producing trioxane are known e.g. homogeneous or heterogeneous acid catalysis of aqueous formaldehyde solutions—from AT 252913—or heterogeneous gas phase catalysis on heteropolyacids—from EP 0606056. Irrespective of the preparation methods, trioxane is produced not as a pure substance, but in a mixture with formaldehyde and small amounts of other components (e.g. methanol, water, methyl formate, methylal, formic acid, dioxolane, tetroxane). To use the trioxane in the polymerization, it is separated, in particular, from the formaldehyde and should contain only small amounts of minor components.

A multiplicity of literature references is known where the objective is to separate aqueous mixtures of formaldehyde and trioxane. The separation of gaseous mixtures comprising the abovementioned components has been described in only a few citations.

The separation from the aqueous solution has hitherto been effected in particular via rectification (AT 252913 (D1)). In the course of the rectification, unreacted formaldehyde is often recycled into the reactor and there continues to be converted into trioxane, as a result of which the conversion of the reaction, based on the formaldehyde, is increased. A limit to the rectification is encountered as a result of an azeotropic mixture, boiling at 92° C. and 1 bar, with water which may be present in various amounts in the starting mixture.

To avoid solids being formed as a result of polymerization of pure formaldehyde or the formation of paraformaldehyde, all those parts of the equipment which come into contact with pure formaldehyde must either be heated to temperatures >100° C. (at 1 bar of formaldehyde partial pressure) or be wetted with a liquid. In the case of the rectification this relates especially to the overhead condenser and constitutes a major drawback compared with separations which take place only in the liquid phase.

An alternative method for separating formaldehyde and trioxane from aqueous solutions consists in the extraction of the trioxane with organic solvents in which trioxane has a higher physical solubility than has the formaldehyde. These processes have been used exclusively for separating the trioxane from the aqueous phase. Examples of organic extractants which have been used include saturated aliphatic or aromatic hydrocarbons or halohydrocarbons (EP 0583907 (D2)), which are sparingly miscible or immiscible with water. A drawback of the extraction is that in some instances major fractions of trioxane remain in the aqueous phase. Large amounts therefore have to be recycled or are lost in the working-up process.

To separate gaseous mixtures of formaldehyde and trioxane, use has been made on a number of occasions of the selective absorption of a species. This either involved, in general, chemisorption of the formaldehyde, the trioxane being left in the gas phase (GB 12459903 (D3)), or conversely a selective physisorption of the trioxane (EP 0680959 (D4)). Since no liquid phase has been found in which either the formaldehyde only or the trioxane only is soluble, some proportion of the respective other species will also be bound. Consequently it is not possible, using this method, to achieve the purity levels required for the polymerization. Furthermore, it gives rise to major losses of the valuable substance trioxane.

A further option described for selective separation from an aqueous phase is the crystallization of the trioxane. This method was employed for separating the trioxane from aqueous formaldehyde-trioxane mixtures (DE 3508668 (D5)), the trioxane concentration in the aqueous mixture being required to exceed 50 wt %, however.

Given this prior art, it is an object of the invention to provide a method which permits the separation of trioxane from a gaseous mixture preferably with formaldehyde, in which the disadvantageous irreversible formation of solid paraformaldehyde is to be avoided.

Those gas/liquid equilibria in the absorption which are nonspecific in terms of the trioxane/formaldehyde separation are not to be utilized for the separation, owing to the low yields to be expected.

This object is to be achieved according to the invention by at least some of the formaldehyde and the trioxane being dissolved from the mixture in a alcohol-containing liquid and the trioxane being crystallized and separated from the solution thus obtained.

The present invention therefore relates to a method for separating a gaseous mixture comprising formaldehyde and trioxane, wherein at least some of the formaldehyde and the trioxane are dissolved from the mixture in a alcohol-containing liquid and the trioxane is crystallized from the solution thus obtained and is separated.

Preferred embodiments are disclosed in the dependent claims.

The gaseous mixture can comprise at least 50 wt % of formaldehyde (FA) and trioxane (TOX) and, at concentrations close to 100 wt % of (FA+TOX) may contain only small amounts of minor components. It is treated in a suitable manner with an alcohol-containing liquid, preferably an alcohol which can be mono- or polyhydric, i.e. a proportion of trioxane and formaldehyde of at least 50% is dissolved, i.e. sorbed, at temperatures in the range from −20 to 100° C., preferably in the range from 20 to 80° C. More preferably, at least 80%, and most preferably almost the entire fraction, i.e. more than 95%, is dissolved. Examples of minor components which can occur in the gas mixture are water, methanol, methyl formate, tetroxane, dioxolane and traces of formic acid. Dissolving the gas in liquid alcohol effectively suppresses the formation of solid paraformaldehyde. Owing to a known chemisorption process (formation of a hemiformal), the absorption capacity for formaldehyde is virtually unlimited. The separation of the TOX, which is physisorbed, can then take place in the method according to the invention by crystallization at temperatures in the range of from −20 to 63° C., preferably in the temperature range of from −10 to 55° C.

In contrast to D5, the method according to the invention achieves the object of separating the mixture of the type produced after the trimerization of formaldehyde having a low water content, the mixture being present in the form of a low-humidity gas and containing formaldehyde and trioxane. The method thus forms a significant step in a process for producing trioxane from methanol, comprising the steps of nonoxidative dehydrogenation (DE 3920811), formaldehyde trimerization (EP 0606056, EP 0691388) and the separation of trioxane (here). Since the advantage of the novel process overall is the production of trioxane at low water levels, D5 does not, in the present case, represent a suitable solution.

In contrast to D3 and D4, both formaldehyde and trioxane can be absorbed completely in the method according to the invention, preference being given to the use of a monohydric alcohol, e.g. cyclohexanol, methanol, propanol, butanol. Alternatively, however, other alcohols, including polyhydric alcohols (e.g. glycerol, diethylene glycol, triethylene glycol, triethanolamine, butanetriol, pentanetriol) can also be used.

Compared with the methods employed hitherto, the method according to the invention in this context is distinguished by the following advantages:

no formation of solids caused by paraformaldehyde owing to the chemisorption of the formaldehyde/trioxane mixture in the liquid phase, high absorption capacity owing to the alcohol used as the absorbent, both for formaldehyde and for trioxane, favorable ratios of recycled trioxane mass flows to the output mass flow, high purities and yields of trioxane achievable by crystallization, favorable ratio of energy input to the amount of trioxane produced.

The method according to the invention is illustrated below with reference to a few experimental studies and FIGS. 1 and 2. This is not intended to constitute any limitation whatsoever.

Figure 2:
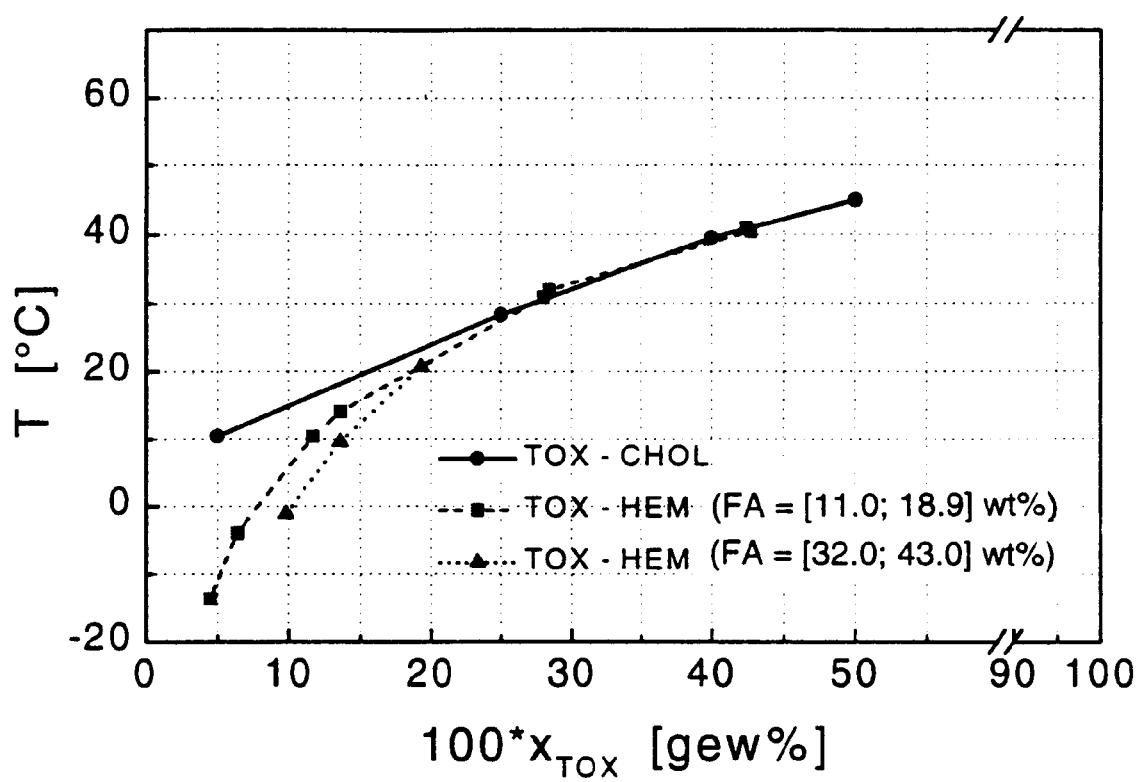

In the drawings:

FIG. 1: shows a process diagram for the pilot plant for the experiments carried out;

FIG. 2: shows solidification curves for trioxane in cyclohexanol or cyclohexyl hemiformal at various formaldehyde levels.

To study the absorption of the gaseous mixture of formaldehyde and trioxane, experiments were carried out using the apparatus outlined in FIG. 1. Via a pump P1, liquid trioxane (TOX) is mixed with a carrier gas stream of nitrogen and is delivered to a cracking reactor R. There the trioxane is evaporated and is cracked in the gas phase, by heterogeneous catalysis on heteropolyacids $(VO(HPO)_4)$ to produce formaldehyde. The conversion achieved in the process can be adjusted over wide limits via the temperature, thus also allowing the ratio of trioxane and formaldehyde at the reactor outlet to be adjusted. Via heated lines R1, the gaseous mixture thus generated is introduced into a stirred vessel R2 which is charged with 0.5 kg of cyclohexanol. The vessel is stirred at a speed of 2000 rpm by means of a sparging mixer and is thermostatted at various temperatures by means of a double jacket. The liquid contents are also passed via a recycling means P2 so that samples can be drawn from this circuit to analyze the liquid phase. The analysis of the gas phase composition was carried out on-line by means of a gas chromatograph GC.

The parameters and results of the experiments carried out on the absorption are summarized in Table 1 below, various compositions of the introduced gas stream and various temperatures of the liquid phase, i.e. the alcohol introduced as an initial charge, being studied. The results show that a major portion (from 80 to 95%) of the mass flow is absorbed, both in terms of formaldehyde and of trioxane.

Table 1: Results of the experiments on the absorption of the gaseous mixture of formaldehyde (FA) and trioxane (TOX).

TABLE 1

Results of the experiments on the absorption of the gaseous mixture of formaldehyde (FA) and trioxane (TOX).

| No. | T [° C.] | Conc. FA in [wt %] | Conc. TOX in [wt %] | Conc. of $N_2$ [wt %] | Ratio FA: TOX | Absorption FA [%] | Absorption TOX [%] |
|-----|----------|--------------------|---------------------|------------------------|---------------|-------------------|--------------------|
| 1A  | 30       | 31.2               | 51.5                | 17.3                   | 0.61          | 97.3              | 95.7               |
| 2A  | 50       | 64.2               | 13.8                | 22.0                   | 4.65          | 96.5              | 65.1               |
| 3A  | 80       | 30.6               | 49.8                | 19.6                   | 0.62          | 80.5              | 90.1               |

It can be seen from Table 1 that the amount of gas absorbed in the experiments is reduced as the temperatures T of the liquid phase increase. At equilibrium, the sorbed fraction of the formaldehyde and trioxane feed is the higher, the lower the temperature and the higher the concentration of these components.

In the method according to the invention, the absorption can be carried out continuously or batchwise, but preferably continuously. The gases to be sorbed can be made to flow cocurrently or countercurrently with respect to the absorbent. The physical implementation, in terms of equipment, of this substep of the method according to the invention can make use of stirred vessels, columns with various internals (e.g. packings, packing elements, trays) or bubble columns.

Formation of trioxane-rich solids as a result of crystallization can take place in the same apparatus as the absorption, although these two steps are preferably carried out separately. The pressure is noncritical for the formation of solids. The temperature chosen for the liquid phase should be as low as possible, to promote absorption (cf. Table 2), but should be high enough, if absorption and crystallization are not carried out in the same apparatus, for trioxane not yet to crystallize out for a given trioxane concentration. The interrelationship between the temperature and the trioxane concentration at which the trioxane just starts to crystallize, is given by the solidification curve or liquidus curve.

Further experiments were carried out to study the precipitation of trioxane as a solid from solutions of cyclohexanol or cyclohexyl hemiformal (formed by chemisorption of formaldehyde in cyclohexanol) and trioxane. It is found that one of the factors determining the shape of the liquidus line in the system trioxane—alcohol/formaldehyde or trioxane-hemiformal is the formaldehyde concentration. As a result of these experiments, three liquidus curves are measured, each for a different formaldehyde concentration, as shown in FIG. 2.

FIG. 2 illustrates that as the formaldehyde concentration in the alcohol or in the hemiformal increases, the liquidus line is shifted towards lower temperatures.

By way of example, further experiments were carried out on the crystallization of the trioxane from a cyclohexyl hemiformal solution. To this end, a thermostatted tube of the type used routinely to study crystallization was filled with the corresponding mixture of substances. By means of a programmable thermostat the jacket temperature was altered at various gradients.

In so doing, a mixture of trioxane and cyclohexanol/ cyclohexyl hemiformal as the starting solution was cooled using a linear temperature gradient. After an end temperature had been reached, the remaining mother liquor was drained off. Then the crystallization tube was heated slowly, and the foot oil resulting from differential melting of the crystallizate upon heating was drained. At the end of the experiment, all remaining crystals were melted. This residual melt is hereinafter referred to as the end fraction.

The results of experiments carried out by way of example are briefly explained below.

EXPERIMENT 1K

In the first experiment, 210.43 g of a starting solution (24.8 wt % of trioxane, 26.4 wt % of formaldehyde, 47.7 wt % of cyclohexyl hemiformal, the remainder being methanol, water) were cooled from 30° C. to −5° C. at a linear temperature gradient of −0.1 K/min. The temperature of −5° C. was maintained over a prolonged period, and finally the mother liquor was drained off.

The mixture remaining in the vessel was then heated to 65° C. at a constant heating rate of 0.11 K/min. At discrete intervals, the liquid sweated off was drawn off as a number of intermediate fractions. At 65° C. the residual mixture had melted completely and was drained off as the end fraction.

The trioxane content in the end fraction was 93.8 wt %. 51.4% of the amount of trioxane used was recovered in the end fraction. The formaldehyde content in the end fraction was 2.3 wt %.

EXPERIMENT 2K

In a second experiment, 179.3 g of a starting solution (24.8 wt % of trioxane, 26.4 wt % of formaldehyde, 47.7 wt % of cyclohexyl hemiformal, the remainder being methanol, water) were cooled from 40° C. to −10° C. at a cooling rate of −0.05 K/min. The temperature of −10° C. was maintained over a prolonged period, and finally the mother liquor was drained off.

The mixture remaining in the vessel was then heated to 65° C. at a heating rate of 0.16 K/min. At various temperatures, the volumes of liquid sweated off in the process were drawn off at specific times as intermediate fractions. At 65° C. the residual mixture had melted completely and was drained off as the end fraction.

The trioxane content in the end fraction was 52.5 wt %. 83.2% of the amount of trioxane used was recovered in the end fraction. The formaldehyde content in the end fraction was 17.0 wt %.

EXPERIMENT 3K

In the third experiment, 144.7 g of a starting solution (26.2 wt % of trioxane, 26.3 wt % of formaldehyde, 47.2 wt % of cyclohexyl hemiformal, the remainder being methanol, water) were cooled from 25° C. to −5° C. at a cooling rate of 0.1 K/min. The temperature of −5° C. was maintained over a prolonged period, and finally the mother liquor was drained off.

The mixture remaining in the vessel was then heated to 65° C. at a heating rate of 0.6 K/min. At discrete intervals, the liquid sweated off was drawn off as a number of intermediate fractions. At 65° C. the residual mixture had melted completely and was drained off as the end fraction.

The trioxane content in the end fraction was 97.7 wt %. 25.6% of the amount of trioxane used was recovered in the end fraction. The formaldehyde content in the end fraction was 0.8 wt %.

EXPERIMENT 4K (stirred)

In a fourth experiment, 50.0 g of a starting solution (35.2 wt % trioxane, 16.0 wt % formaldehyde, 48.1 wt % cyclohexyl hemiformal, the remainder being methanol, water) were stirred in a double-jacket vessel equipped with a magnetic stirrer. Via the double jacket, the starting solution was cooled from 35° C. to 100° C. at 0.2 K/min. In the process, the trioxane crystallized out as an acicular crystallizate. From the suspension, vary small amounts of sample were examined microscopically and the diameter of the crystal needles was found to be about 100 μm. The length was irregular.

Finally, all of the suspension was drained from the stirred vessel at the temperature of 10° C. and was filtered via a sintered disk to whose filtrate side a vacuum of 200 mbar was applied.

The filtrate (mother liquor) and the filter cake (crystal fraction) were then analyzed. The trioxane content in the crystal fraction was 76.8 wt %. The formaldehyde content in the crystal fraction was 5.8 wt %. In the mother liquor, 19.1% of the trioxane used was recovered. This meant that 80.9% of the trioxane used remained in the crystal fraction.

EXPERIMENT 5K (stirred)

In a fifth experiment, 1000.0 g of a starting solution (35.7 wt % trioxane, 16.8 wt % formaldehyde, 46.8 wt % cyclohexyl hemiformal, the remainder being methanol, water) were stirred in a double-jacket vessel equipped with a magnetic stirrer at 200 min$^{-1}$. Via the double jacket, the starting solution was cooled from 33° C. to 50° C. at 0.2 K/min. In the process, the trioxane crystallized out as an acicular crystallizate. From the suspension, very small amounts of sample were examined microscopically and the diameter of the crystal needles was found to be about 100 μm. The length was irregular.

Finally, all of the suspension was drained from the stirred vessel at the temperature of 5° C. and was filtered via an open-bottom basket centrifuge.

The filtrate (mother liquor) and the filter cake (crystal fraction) were then analyzed. The trioxane content in the crystal fraction was 85.9 wt %. The formaldehyde content in the crystal fraction was 3.5 wt %. In the mother liquor, the trioxane concentration was 9.2 wt %.

The preferred approach suggesting itself for the purpose of a continuous process involves a modification of the implementation described in Experiments 4 and 5. An example of a stirring apparatus suitable for this purpose is a scraped-surface cooler which continuously scrapes off crystals accreted on the walls and thus promotes heat transfer to the wall. The scraped-surface cooler can advantageously be combined with a stirred vessel operated adiabatically, in which the crystals from the liquid supercooled in the scraped-surface cooler are able to grow.

The combination of scraped-surface cooler and adiabatic stirred vessel is continuously fed with liquid solution adjusted to conditions above the liquidous curve, and at the outlet of the apparatus a suspension containing trioxane crystals is continuously drawn off.

By means of solid-liquid separation methods, the solid (trioxane crystals) is separated from the suspension drawn off. Examples of solid-liquid separation methods include filter nutsches, belt filters, centrifuges but also any other methods.

Reference symbol list for FIG. 1:

| | |
|---|---|
| P1 | pump for delivering TOX and N$_2$ |
| P2 | circulation pump |
| R | cracking reactor |

-continued

| | |
|---|---|
| R1 | heated line |
| R2 | stirred vessel |
| T1, T2 | thermostat |
| V1, V2, V3 | valve/shut-off valve |
| E1 | exhaust |
| E2 | sampling |

What is claimed is:

1. A method for separating a gaseous mixture comprising formaldehyde and trioxane, wherein at least some of the formaldehyde and the trioxane are dissolved from the mixture in a alcohol-containing liquid and the trioxane is crystallized from the solution thus obtained and is separated.

2. The method as claimed in claim 1, wherein the proportion of formaldehyde and trioxane in the mixture is at least 50 wt % and wherein at least 50% of said proportion is dissolved in the alcohol-containing liquid.

3. The method as claimed in claim 1, wherein the dissolution of formaldehyde and trioxane in an alcohol-containing liquid takes place at temperatures in the range of from −20 to +100° C.

4. The method as claimed in claim 1, wherein the alcohol-containing liquid contains as a solvent at least one mono- or polyhydric alcohol.

5. The method as claimed in claim 1, wherein the crystallization of the trioxane takes place at temperatures in the range of from −25 to 63° C.

6. The method as claimed in claim 1, wherein the crystallization of the trioxane takes place by cooling while the solution is at rest.

7. The method as claimed in claim 1, wherein the trioxane crystallizate is formed at cold walls while the solution is recycled.

8. The method as claimed in claim 1, wherein the trioxane crystallizate is generated in the form of a suspension while the solution is stirred.

9. The method as claimed in claim 8, wherein the trioxane crystallizate is separated off by means of sedimentation in the gravity field of the Earth or in a centrifugal force field.

10. The method as claimed in claim 8, wherein the trioxane crystallizate is separated off by means of a filtration.

* * * * *